(12) United States Patent
Nakahara et al.

(10) Patent No.: US 6,649,787 B1
(45) Date of Patent: Nov. 18, 2003

(54) METHOD FOR PREPARING (METH) ACRYLIC ACID ESTER

(75) Inventors: Sei Nakahara, Himeji (JP); Masatoshi Ueoka, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 36 days.

(21) Appl. No.: 09/684,396

(22) Filed: Oct. 10, 2000

(30) Foreign Application Priority Data

Oct. 12, 1999 (JP) .......................................... 11-289345

(51) Int. Cl.[7] ........................... C07C 69/52; C07C 67/48
(52) U.S. Cl. ...................................................... 560/205
(58) Field of Search ................................. 560/205, 218

(56) References Cited

U.S. PATENT DOCUMENTS

| | | | | |
|---|---|---|---|---|
| 4,250,328 A | * | 2/1981 | Fujita et al. | 560/205 |
| 4,956,493 A | | 9/1990 | Ueoka et al. | 560/208 |
| 6,482,976 B1 | * | 11/2002 | Ho et al. | 560/205 |

FOREIGN PATENT DOCUMENTS

WO          9852904          11/1998

* cited by examiner

Primary Examiner—Mukund J. Shah
Assistant Examiner—Zachary C. Tucker
(74) Attorney, Agent, or Firm—Sherman & Shalloway

(57) ABSTRACT

An improvement is provided in a method for preparing an (meth)acrylic acid ester comprising an esterification step for forming the (meth)acrylic acid ester by esterification reaction between (meth)acrylic acid and the corresponding aliphatic alcohol having 1 to 4 carbon atoms in the presence of an acidic catalyst, and a separation-purification step comprising an acid-separating column, a low boiling matter-separating column and a rectification column for separating and purifying the (meth)acrylic acid ester from the (meth) acrylic acid ester-containing mixture obtained in the esterification step. This improvement lies in that by circulating the bottom residue of the rectification column into the esterification step and/or the separation-purification step, the remaining polymerization inhibitor in the bottom residue is effectively reused and the remaining (meth)acrylic acid ester in the bottom residue is efficiently recovered.

1 Claim, 1 Drawing Sheet

METHOD FOR PREPARING (METH) ACRYLIC ACID ESTER

TECHNICAL FIELD TO WHICH THE INVENTION PERTAINS

This invention relates to a method for preparing a (meth) acrylic acid ester. More detailedly, this invention relates to an improvement in a method for preparing a (meth)acrylic acid ester comprising an esterification step for carrying out esterification reaction between (meth)acrylic acid and an alcohol, and a separation-purification step comprising an acid-separating column, a low boiling matter-separating column and a rectification column for separating and purifying the (meth)acrylic acid ester from the (meth)acrylic acid ester-containing mixture obtained in the esterification step, and the improvement lies in circulating the bottom residue of the rectification column into the esterification step and/or the separation-purification step, and thereby effectively reusing the polymerization inhibitor still remaining in the bottom residue and efficiently recovering the (meth) acrylic acid ester still remaining in the bottom residue.

PRIOR ART

It is industrially carried out to prepare a (meth)acrylic acid ester by esterifying (meth)acrylic acid and the corresponding aliphatic alcohol having 1 to 4 carbon atoms in the presence of an acidic catalyst, and separating and purifying the (meth)acrylic acid ester from the resulting esterification reaction mixture.

As methods for separating and purifying the (meth)acrylic acid ester from the esterification reaction mixture, for example, a method for obtaining a highly pure (meth)acrylic acid ester by separating and purifying the (meth)acrylic acid ester using an apparatus composed of an alcohol-recovering column, a low boiling matter-separating column and a high boiling matter-separating column is described in Japanese Patent Publication No. 7-64787.

PROBLEM TO BE SOLVED BY THE INVENTION

It goes without saying that it is industrially desirable to prepare a (meth)acrylic acid ester in a high yield and prepare a (meth)acrylic acid ester economically advantageously by reducing the preparation costs of the (meth)acrylic acid ester.

Therefore, the object of the invention lies in providing a method for preparing a (meth)acrylic acid ester in a high yield and economically advantageously.

MEANS FOR SOLVING THE PROBLEM

The present inventors have re-examined the method described in the Japanese Patent Publication No. 7-64787, and as a result they have found that the polymerization inhibitor contained in the bottom residue of the high boiling matter-separating column in the method is not largely denatured, and therefore that the bottom residue can be reused by circulating it as such into the esterification step and the separation-purification step, and thereby that the (meth)acrylic acid ester can be obtained in a high yield. The invention was completed based on these findings. It is a discovery made for first time by the present inventors that the polymerization inhibitor contained in the bottom residue is not largely denatured.

Thus, according to the invention is provided in a method for preparing an (meth)acrylic acid ester comprising an esterification step for forming the (meth)acrylic acid ester by esterification reaction between (meth)acrylic acid and the corresponding aliphatic alcohol having 1 to 4 carbon atoms in the presence of an acidic catalyst, and a separation-purification step comprising an acid-separating column, a low boiling matter-separating column and a rectification column for separating and purifying the (meth)acrylic acid ester from the (meth)acrylic acid ester-containing mixture obtained in the esterification step, the improvement comprising circulating the bottom residue of the rectification column into the esterification step and/or the separation-purification step.

MODE FOR CARRYING OUT THE INVENTION

In the attached drawings, FIG. 1 is a flow sheet showing an embodiment of the method of the invention, and FIG. 2 is a flow sheet showing another embodiment.

BRIEF DESCRIPTION OF THE DRAWINGS

In FIG. 1 and FIG. 2, 1, 2, 3, 4 and 5 show an esterifying reactor, an acid-separating column, a low boiling matter-separating column, a rectification column and high boiling matter-separating column, respectively.

Figure 1:
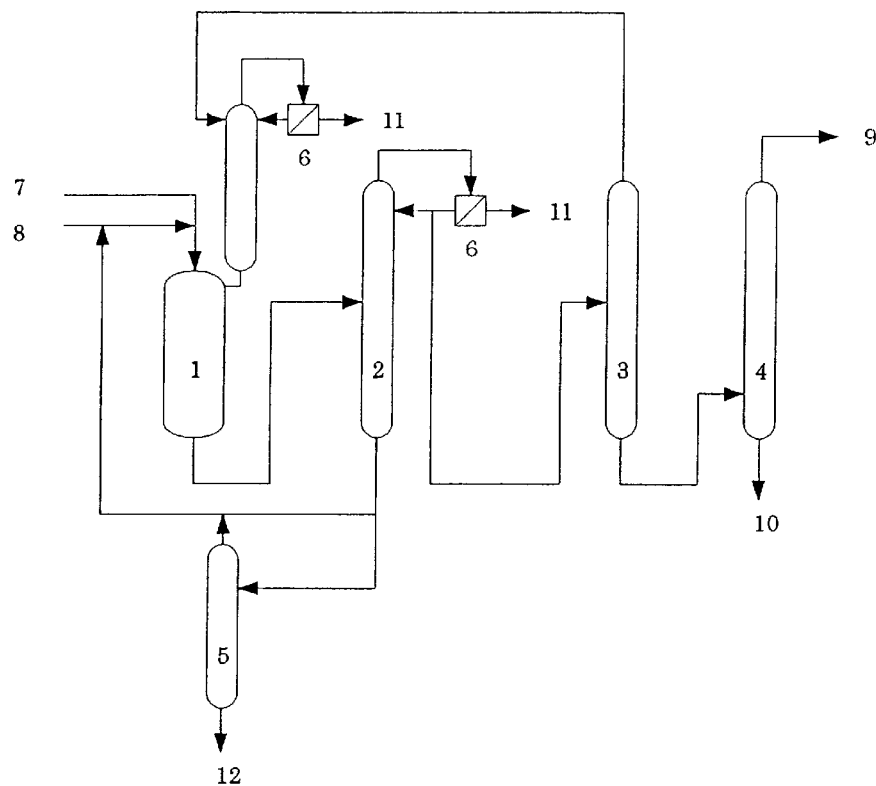

The invention is specifically described taking the embodiment shown in FIG. 1 as an example.

In the esterifying reactor 1, (meth)acrylic acid and an aliphatic alcohol having 1 to 4 carbon atoms (e.g., methanol, ethanol, etc.) are fed for esterification reaction in the presence of an acidic catalyst (e.g., a strongly acidic cation exchange resin, etc.) to prepare the corresponding (meth) acrylic acid ester. The mixture containing the (meth)acrylic acid ester obtained in the esterifying reactor 1 (this mixture is referred to as a (meth)acrylic acid ester-containing mixture in the invention) is introduced into the acid-separating column 2, and the (meth)acrylic acid ester is separated there and a mixture containing the (meth)acrylic acid ester, the unreacted alcohol, water, etc. is recovered from the column top. Then, the mixture is separated into an oil phase and a water phase in the oil-water separator 6, and the oil phase is introduced into the low boiling matter-separating column 3, and, there, part of the (meth)acrylic acid ester, the unreacted alcohol, water, etc. are distilled and the crude (meth)acrylic acid ester is recovered from the column bottom. This crude (meth)acrylic acid ester is fed to the rectification column 4, and the product (meth)acrylic acid ester is recovered from the column top. Then, the bottom residue of this column is circulated for example into the acid-separating column 2 or the low boiling matter-separating column 3 for effectively reusing the still active polymerization inhibitor contained therein.

The characteristic of the invention lies in circulating part or whole of the bottom residue from the rectification column 4 into any spot of the esterification step and/or the separation-purification step, specifically into any one or two or more of the esterifying reactor 1, the acid-separating column 2, the low boiling matter-separating column 3, the rectification column 4 and the high boiling matter-separating column 5. Thereby, the polymerization inhibitor contained in the bottom residue from the rectification column 4 can be reused for polymerization inhibition in the esterification step and the separation-purification step. Thus, since the amount of the new polymerization inhibitor used in the esterification step and the separation-purification step can be reduced and moreover the (meth)acrylic acid ester contained in the bottom residue can effectively be recovered, it gets possible to prepare the (meth)acrylic acid ester in a high yield.

As the polymerization inhibitor, ones generally used in this kind of reaction can be used. For example, hydroquinone, phenothiazine, t-butylcatechol, p-benzoquinone, hydroquinone monomethyl ether, Methylene Blue, diphenylamine, N-oxyl compounds such as 4-hydroxy-2,2,6,6-tetramethylpiperidinooxyl, etc. can be used alone or as a mixture of two or more of them.

Figure 2:
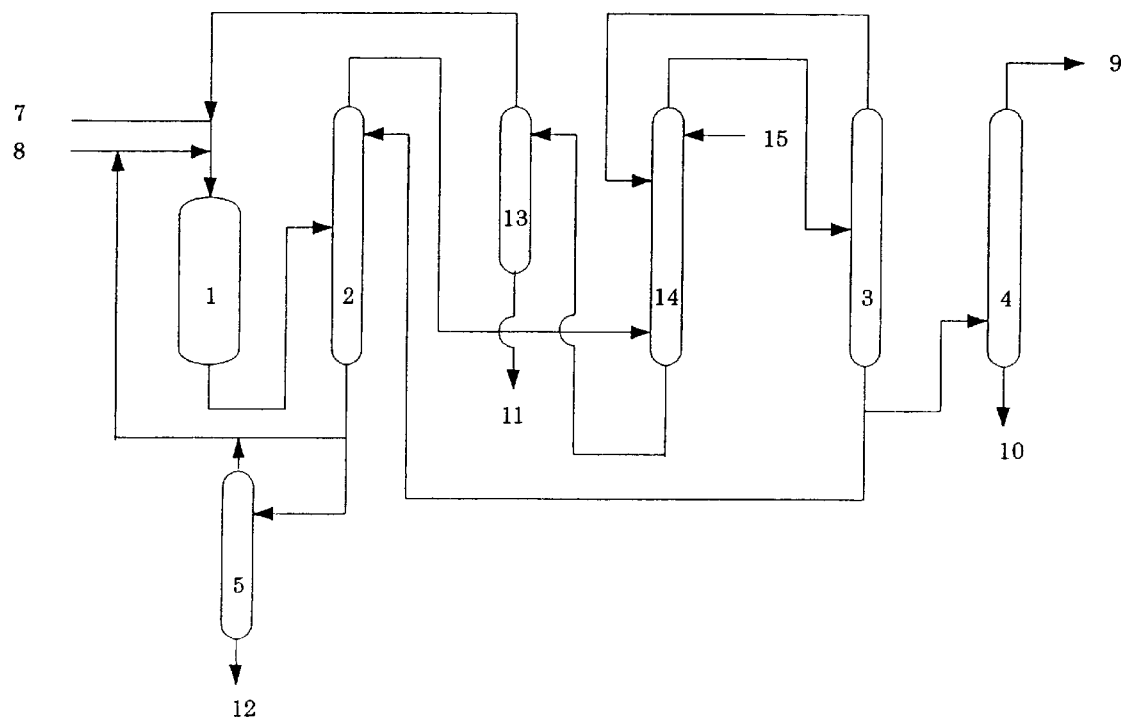

In the embodiment shown in FIG. 2, an extracting column 14 is placed. Into this extracting column 14 is introduced the mixture containing the (meth)acrylic acid ester, the unreacted alcohol, water, etc. from the acid-separating column 2, water is extracted there, and the resulting oil phase is introduced into the low boiling matter-separating column 3. The crude (meth)acrylic acid ester obtained in the low boiling matter separating column 3 is introduced into the rectification column 4, and the product (meth)acrylic acid ester is recovered from the column top. Then, for reusing the polymerization inhibitor, the bottom residue of this column is circulated into any spot of the esterification step and the separation-purification step (but excluding the extracting column 14), specifically into any one or two or more of the esterifying reactor 1, the acid-separating column 2, the low boiling matter-separating column 3, the rectification column 4 and the high boiling matter-separating column 5.

EFFECT OF THE INVENTION

According to the method of the invention, since the polymerization inhibitor contained in the bottom residue of the rectification column can effectively be recycled, the preparation costs of a (meth)acrylic acid ester can be reduced. Further, since the remaining (meth)acrylic acid ester in the bottom residue can effectively be recovered, the (meth)acrylic acid ester can be prepared in a high yield.

EXAMPLE

The invention is further detailedly described below according to examples.

Example 1

Butyl acrylate was prepared according to a flow sheet shown in FIG. 1.

Acrylic acid containing 0.1% by weight phenothiazine as a polymerization inhibitor at a feeding speed of 0.15 kg/h, n-butanol at a feeding speed of 0.16 kg/h, and a liquid, at a feeding speed of 1.34 kg/h, consisting of 56.2% by weight butyl acrylate, 25.3% by weight acrylic acid, 7.1% by weight n-butanol, 2.0% by weight water and 9.4% by weight phenothiazine-containing high boiling matter which liquid was obtained by mixing the bottom liquid of the acid-separating column 2 with the column top liquid of the high boiling matter-separating column 5 obtained by making the operation introducing part of the bottom liquid were fed to a glass-made esterifying reactor 1 in which a strongly acidic cation exchange resin was put as a catalyst. The n-butanol-containing liquid recovered from the column top of the low boiling matter-separating column 3 was introduced into a distilling column (Dixon Packing packed column) attached to the esterifying reactor 1. By carrying out continuously esterification reaction while removing the reaction-formed water shown by arrow mark 11 which is drawn from oil-water separator 6 attached to esterifying reactor 1 and which points to the right is a purge line for water from the column top, a reaction liquid consisting of 60.2% by weight of butyl acrylate, 20.0% by weight acrylic acid, 9.4% by weight n-butanol, 2.3% by weight water and 8.1% by weight phenothiazine-containing high boiling matter was obtained, at a speed of 1.70 kg/h, at the outlet of the esterifying reactor 1.

The reaction liquid was introduced into the column bottom of the acid-separating column 2 as a glass-made Older-Show type distilling column of inside diameter 50 mm (number of total stages 20), and a mixture comprising butyl acrylate, n-butanol and water, substantially not containing acrylic acid, was distilled from the column top. In this operation, for preventing polymerization in the acid-separating column 2, phenothiazine dissolved in the refluxed liquid was introduced at a speed of 5 g/h.

Then, the distillate from the acid-separating column 2 was separated into an oil phase and a water phase in the oil-water separator 6 attached to the acid-separating column 2, the oil phase was introduced into the low boiling matter-separating column 3 at the 6th stage from the top which column 3 was a glass-made Older-Show type distilling column of inside diameter 32 mm (number of total stages 20) wherein arrow mark 11 which is drawn from oil-water separator 6 attached to acid separating column 2 and which points to the right is a purge line for water. The liquid consisting of 76.1% by weight butyl acrylate, 13.3% by weight n-butanol and 10.6% by weight water recovered from the column top of the low boiling matter-separating column 3 was returned at a speed of 0.08 kg/h to the distilling column attached to the esterifying reactor 1. The crude butyl acrylate substantially not containing n-butanol was withdrawn at a speed of 0.26 kg/h from the column bottom of the low boiling matter-separating column 3, and introduced into the column bottom of the rectification column 4. In this operation, for preventing polymerization in the low boiling matter-separating column 3, phenothiazine dissolved in the refluxed liquid was introduced at a speed of 1 g/h.

A liquid consisting of 55.8% by weight butyl acrylate, 25.1% by weight acrylic acid, 7.0% by weight n-butanol, 2.0% by weight water and 10.1% by weight the phenothiazine-containing high boiling matter was withdrawn at a speed of 1.36 kg/h from the column bottom of the acid-separating column 2. Part of the liquid was introduced into the column top of the high boiling matter-separating column 5 which was a glass-made Older-Show type distilling column of inside diameter 32 mm (number of total stages 5), high boiling matter was discarded from the column bottom, the distillate was returned together with the remaining bottom liquid from the acid-separating column 2 to the esterifying reactor 1 wherein arrow mark 12 which is drawn from the bottom of high boiling matter-separating column 5 and which points downward is a purge line for high boiling matter.

For polymerization inhibition, hydroquinone monomethyl ether dissolved in the refluxed liquid was introduced at a speed of 1 g/h into the rectification column 4 which was a glass-made Older-Show type distilling column of inside diameter 32 mm (number of total stages 10). The product butyl acrylate was obtained at a speed of 0.25 kg/h from the column top of the rectification column 4, and butyl acrylate containing phenothiazine and hydroquinone monomethyl ether was recovered as the bottom residue from the column bottom. Since when this bottom residue was analyzed, 97% and 99% of the introduced phenothiazine and hydroquinone monomethyl ether, respectively, remained, the bottom residue was circulated for reuse as a polymerization inhibitor into the acid-separating column 2 and the low boiling matter-separating column 3.

Example 2

Methyl acrylate was prepared according to a flow sheet shown in FIG. 2.

The combined liquid (total 4.17 kg/h) of acrylic acid (1.00 kg/h) containing 0.1% by weight hydroquinone as a polymerization inhibitor, methanol (0.43 kg/h), the recovered liquid (2.50 kg/h) consisting of the bottom liquid of the acid-separating column 2 and the column top liquid of the high boiling matter-separating column 5 obtained by making the operation introducing part of the bottom liquid and the methanol-containing liquid (0.24 kg/h) recovered from the column top of the alcohol-recovering column 13—the combined liquid consists of 10.8% by weight methyl acrylate, 51.4% by weight acrylic acid, 13.8% by weight methanol, 4.7% by weight water and 19.3% by weight the hydroquinone-containing high boiling matter—was fed to a stainless steel-made esterifying reactor 1 packed with a strongly acidic cation exchange resin as a catalyst. The reaction liquid consisting of 38.0% by weight methyl acrylate, 27.5% by weight acrylic acid, 3.6% by weight methanol, 10.5% by weight water and 20.4% by weight high boiling matter containing hydroquinone was obtained at the outlet of the esterifying reactor 1.

This reaction liquid was introduced into the column bottom of the acid-separating column 2 which was a glass-made Older-Show type distilling column of inside diameter of 50 mm (number of total stages 20), and a mixture substantially not containing acrylic acid and consisting of 90.1% by weight methyl acrylate, 3.3% by weight methanol and 6.6% by weight water was distilled at a speed of 3.93 kg/h from the column top. In this operation, hydroquinone dissolved in the refluxed liquid was introduced at a speed of 2.5 g/h for preventing polymerization in the acid-separating column 2. A liquid consisting of 13.9% by weight methyl acrylate, 44.9% by weight acrylic acid, 0.8% by weight methanol, 7.0% by weight water and 33.4% by weight hydroquinone-containing high boiling matter was withdrawn at a speed of 2.55 kg/h from the column bottom of the acid-separating column 2. Part of the liquid was introduced into the column top of the high boiling matter-separating column 5 which was a glass-made Older-Show type distilling column of inside diameter of 32 mm (number of total stages 5), and high boiling matter was discarded from the column bottom, and the distillate was returned together with the remaining bottom liquid from the acid-separating column 2 to the esterifying reactor 1.

Then, the distillate of the acid-separating column 2 and the distillate from the low boiling matter-separating column 3 consisting of 15.5% by weight methyl acrylate, 4.5% by weight methanol and 80.0% by weight water were introduced at a speed of 0.14 kg/h into a Quni type liquid-liquid extracting column 14 of inside diameter 100 mm, and extraction was carried out with water of a speed of 1.29 kg/h, and thereby an oil phase consisting of 96.7% by weight methyl acrylate, 0.2% by weight methanol and 3.1% by weight water was obtained at a speed of 3.59 kg/h. The water phase was introduced into an alcohol-recovering column 13, and methanol was distilled at a speed of 0.24 kg/h from the column top and circualted into the esterifiing reactor 1. Part of the bottom liquid was reused as water introduced into the extracting column 14.

The oil phase obtained from the extracting column 14 was introduced into the low boiling matter-separating column 3 at the 10th stage from the top which column was a glass-made Older-Show type distilling column of inside diameter of 50 mm (number of total stages 20), and methanol and methyl acrylate were recovered under normal pressure from the column top and returned to the extracting column 14. Crude methyl acrylate substantially not containing methanol obtained from the column bottom was introduced at a speed of 1.14 kg/h into the column bottom of the rectification column 4 except that part of the crude methyl acrylate was used as a refluxing liquid for the acid-separating column 2. In this operation, hydroquinone dissolved in the refluxed liquid was introduced at a speed of 2.5 g/h for preventing polymerization in the low boiling matter separating column 3.

For preventing polymerization, hydroquinone dissolved in the refluxed liquid was introduced at a speed of 2.5 g/h into the rectification column 4 which was a glass-made Older-Show type distilling column of inside diameter of 32 mm (number of total stages 10). The product methyl acrylate was obtained at a speed of 1.09 kg/h from the column top, and methyl acrylate containing hydroquinone was recovered as the bottom residue from the column bottom. Since when the bottom residue was analyzed, 98% of the introduced hydroquinone remained, the bottom residue was circulated into the acid-separating column 2 and the low boiling matter-separating column 3 and reused as a polymerization inhibitor.

What is claimed is:

1. A method for preparing an (meth)acrylic acid ester comprising
   an esterification step for forming the (meth)acrylic acid ester by esterification reaction between (meth)acrylic acid and the corresponding aliphatic alcohol having 1 to 4 carbon atoms in the presence of an acidic catalyst, and
   a separation-purification step consisting of
      one acid-separating column,
      one low boiling matter-separating column and
      one rectification column for separating and purifying the (meth)acrylic acid ester from the (meth)acrylic acid ester-containing mixture obtained in the esterification step,
   characterized in that the whole of the bottom residue of the rectification column is circulated back through the rectification column and optionally at least one of the acid-separating column τ and the low boiling matter-separating column.

* * * * *